(12) United States Patent
Jiang

(10) Patent No.: US 12,365,901 B2
(45) Date of Patent: Jul. 22, 2025

(54) APPLICATION OF MECHANICAL-FORCE SENSITIVE MACROPHAGE SUBSET IN PANCREATIC CANCER DIAGNOSIS OR PROGNOSIS EVALUATION

(71) Applicant: Hong Jiang, Chengdu (CN)

(72) Inventor: Hong Jiang, Chengdu (CN)

( * ) Notice: Subject to any disclaimer, the term of this patent is extended or adjusted under 35 U.S.C. 154(b) by 0 days.

(21) Appl. No.: 18/793,716

(22) Filed: Aug. 2, 2024

(65) Prior Publication Data
US 2025/0171784 A1    May 29, 2025

Related U.S. Application Data

(63) Continuation of application No. PCT/CN2023/133649, filed on Nov. 23, 2023.

(51) Int. Cl.
*C12N 15/113*   (2010.01)
*A61K 39/395*   (2006.01)
*A61P 35/00*    (2006.01)

(52) U.S. Cl.
CPC .... *C12N 15/1137* (2013.01); *A61K 39/39558* (2013.01); *A61P 35/00* (2018.01); *C12Y 207/10002* (2013.01); *C12N 2310/14* (2013.01); *C12N 2320/31* (2013.01)

(58) Field of Classification Search
CPC ............ C12N 15/1137; C12N 2310/14; C12N 2320/31; A61P 35/00; A61K 39/39558; C12Y 207/10002
USPC .............. 435/6.1, 91.1, 91.31, 455, 458; 514/44 A; 530/350; 536/23.1, 24.5
See application file for complete search history.

(56) References Cited

U.S. PATENT DOCUMENTS

| | | | | |
|---|---|---|---|---|
| 2008/0113351 A1* | 5/2008 | Naito | ........................ | A61P 5/26 |
| | | | | 536/23.1 |
| 2009/0312194 A1* | 12/2009 | Tyner | ..................... | C12Q 1/485 |
| | | | | 506/10 |

FOREIGN PATENT DOCUMENTS

| | | | | |
|---|---|---|---|---|
| CN | 110456054 A | 11/2019 | | |
| CN | 111655288 A | 9/2020 | | |
| CN | 111735945 A | 10/2020 | | |
| CN | 113330310 A | 8/2021 | | |
| CN | 114410633 A | 4/2022 | | |
| CN | 114641310 A | 6/2022 | | |
| WO | WO-2004045543 A2 * | 6/2004 | ........... | A61K 31/713 |
| WO | 2015117164 A1 | 8/2015 | | |
| WO | 2022265326 A1 | 12/2022 | | |

OTHER PUBLICATIONS

Internation Search Report of PCT/CN2023/133649, Mailed Jun. 23, 2024.

* cited by examiner

*Primary Examiner* — Jane J Zara

(57) ABSTRACT

Disclosed is an application of a mechanical force sensitive macrophage subset in pancreatic cancer diagnosis or prognosis evaluation, in which it is found that a number of mechanical force sensitive macrophages of CD68$^+$p-PYK2$^+$ YAP1$^+$ in pancreatic cancer is obviously higher than that of an adjacent normal tissue, and the number of the macrophages is in positive correlation with a pancreatic cancer process, so that the mechanical force sensitive macrophages can be used as a pancreatic cancer diagnosis and prognosis index. An elasticity modulus of the cells is reduced by inhibiting a mechanical force check point PYK2 of monocytes/macrophages, and differentiation of the monocytes into the macrophages is inhibited, so that a tumor microenvironment of the pancreatic cancer is improved. Growth of the pancreatic cancer is remarkably inhibited through combined treatment, and the lifetime of mice with the pancreatic cancer is remarkably prolonged.

3 Claims, 17 Drawing Sheets

Specification includes a Sequence Listing.

APPLICATION OF MECHANICAL-FORCE SENSITIVE MACROPHAGE SUBSET IN PANCREATIC CANCER DIAGNOSIS OR PROGNOSIS EVALUATION

CROSS-REFERENCE TO RELATED APPLICATIONS

This application is a continuation of International Patent Application No. PCT/CN2023/133649 with a filing date of Nov. 23, 2023, designating the United States, now pending. The content of the aforementioned applications, including any intervening amendments thereto, are incorporated herein by reference.

TECHNICAL FIELD

The present invention relates to the technical field of tumor prognosis evaluation, and particularly to an application of a mechanical force sensitive macrophage subset in pancreatic cancer diagnosis or prognosis evaluation.

SEQUENCE LISTING

The present application contains a sequence listing which was filed electronically in XML format and is hereby incorporated by reference in its entirety. Besides, the XML copy is created on Sep. 28, 2024, is named "APPLICATION OF MECHANICAL-FORCE SENSITIVE MACROPHAGE SUBSET IN PANCREATIC CANCER DIAGNOSIS OR PROGNOSIS EVALUATION-Sequence Listing" and is 11,453 bytes in sizes.

BACKGROUND OF THE PRESENT INVENTION

Pancreatic cancer is a highly fatal disease, with hidden onset, difficult early diagnosis, rapid progress, easy metastasis and poor prognosis. Although the use of conventional chemotherapy in the pancreatic cancer has made progress, a 5-year survival rate is less than 9% (Siegel, R. L., et. al., Cancer statistics, 2019. CA Cancer J Clin, 2019. 69(1): 7-34), and the pancreatic cancer is expected to become the second leading cause of cancer death by 2030 (Cronin, K. A., et. Al., Annual Report to the Nation on the Status of Cancer, part I: National cancer statistics. Cancer, 2018. 124(13): 2785-2800).

The pancreatic cancer lacks early manifestations, so that it is a challenge to make accurate clinical diagnosis. At present, detection indexes such as CA19-9 and CA125 of commonly used pancreatic cancer markers can be increased in bodies of some patients, so that the detection indexes cannot accurately reflect conditions of the patients, thus leading to misdiagnosis and missed diagnosis. Surgical resection is a main treatment for the pancreatic cancer. In recent years, despite the continuous progress in the surgical resection and drug treatment of the pancreatic cancer, a mortality rate of patients with the pancreatic cancer remains high (Brahmer, J. R., et al., Safety and activity of anti-PD-L1 antibody in patients with advanced cancer. The New England journal of medicine, 2012. 366(26): 2455-2465). Therefore, it is urgent to develop a new diagnosis and treatment method for the pancreatic cancer.

One of characteristics of the pancreatic cancer is that there are a dense connective tissue and high fibrosis in a pancreatic tissue (Whatcott, C. J., et al., Desmoplasia in Primary Tumors and Metastatic Lesions of Pancreatic Cancer. Clinical cancer research: an official journal of the American Association for Cancer Research, 2015. 21(15): 3561-3568), thus forming a high-rigidity physical microenvironment of the pancreatic cancer. Therefore, a high-rigidity elastic modulus of the pancreatic cancer tissue may become a diagnostic index of the pancreatic cancer.

An immunosuppressive tumor microenvironment is one of main obstacles in the treatment of the pancreatic cancer, wherein tumor-associated macrophages are one of most abundant immunosuppressive cells and play an important role in promoting tumor progression (Christofides A., et. al., The complex role of tumor-infiltrating macrophages. Nature Immunology, 2022, 23: 1148-1156). The high-rigidity physical microenvironment may activate a mechanical force signal pathway of monocytes/macrophages, thus promoting the formation of the tumor-associated macrophages. Therefore, it is very important to find a checkpoint of mechanical force signal for regulating and controlling differentiation and polarization of the monocytes/macrophages. Meanwhile, the detection of monocytes/macrophages with mechanical force signal response may be used as a method for diagnosis, treatment evaluation and prognosis of the pancreatic cancer.

Proline-rich tyrosine kinase (PYK2) is a non-receptor tyrosine kinase and an important member of focal adhesion kinase, and participates in many physiological and pathological processes, comprising cell adhesion, cell migration, inflammatory reaction, tumor infiltration, and the like (Ryzhakov, G., et. al., Defactinib inhibits PYK2 phosphorylation of IRF5 and reduces intestinal inflammation. Nature Communications, 2021, 12: 6702; Müller, A. K., et. al., Mouse Modeling Dissecting Macrophage-Breast Cancer Communication Uncovered Roles of PYK2 in Macrophage Recruitment and Breast Tumorigenesis. Advanced Science, 2022, 9: 2105696). In the macrophages, the PYK2 is located in a podosome of the macrophages, may participate in regulating and the controlling the cell adhesion, morphology and migration of the macrophages (Duong, L. T. and Rodan G. A., PYK2 is an adhesion kinase in macrophages, localized in podosomes and activated by beta (2)-integrin ligation, Cell Motil Cytoskeleton, 2000, 47(3):174-88; Okigaki, M., Pyk2 regulates multiple signaling events crucial for macrophage morphology and migration. PNAS, 2003, 100 (19):10740-10745). The macrophages are differentiated from the monocytes. Previous studies believe that a differentiation process of the monocytes/macrophages is mainly regulated and controlled by cytokines (such as M-CSF and PMA), and other biochemical signals, and whether and how mechanical signals participate in the differentiation of the monocytes/macrophages is unknown. Although the PYK2 is highly expressed and activated in the differentiation and polarization of the monocytes/macrophages, whether the PYK2 can be used as a mechanical force checkpoint to regulate and control the perception and response of the monocytes/macrophages to an external physical microenvironment has not been reported, a mechanical force signal pathway involved in the PYK2 is still unclear, and the role of the PYK2 as the mechanical force checkpoint of the monocytes/macrophages in the diagnosis and treatment of the pancreatic cancer is even less studied.

SUMMARY OF THE PRESENT INVENTION

In view of this, a first object of the present invention is to provide an application of a mechanical force sensitive macrophage subset in pancreatic cancer diagnosis or prognosis evaluation; a second object of the present invention is to provide an application of a reagent for detecting the mechanical force sensitive macrophage subset in preparation of a product for pancreatic cancer diagnosis or prognosis evaluation; a third object of the present invention is to provide a function of a reagent for targeted inhibition or knock out of mechanical force response signal PYK2 expression in reducing an elastic modulus of cells or inhibiting differentiation of monocytes into macrophages; and a fourth object of the present invention is to provide an application of a PYK2 inhibitor in combination with a PD-1 immunosuppressant in preparation of a drug for treating pancreatic cancer.

In order to achieve the above objects, the present invention provides the technical solutions as follows.

1. An application of a mechanical force sensitive macrophage subset in pancreatic cancer diagnosis or prognosis evaluation is provided, wherein the mechanical force sensitive macrophage subset is labeled as $CD68^+p\text{-}PYK2^+YAP1^+$ or $CD68^+CD206^{+p\text{-}PYK}2^+YAP1^{+p\text{-}MLC}2^+$ on a cell surface on a protein level.

According to the present invention, preferably, in detection results, when a proportion of the mechanical force sensitive macrophage subset in total cells is higher, a possibility of pancreatic cancer is higher, or a prognosis effect is worse.

2. An application of a reagent for detecting the mechanical force sensitive macrophage subset in preparation of a product for pancreatic cancer diagnosis or prognosis evaluation is provided.

According to the present invention, preferably, the reagent for detecting the mechanical force sensitive macrophage subset comprises one or more immunoreagents of CK19, CD68, YAP1, FAP, COL1A1, p-PYK2, Lamin A/C, p-MLC2, Ki67, Lyve1, CD206, CD8 and CD3.

According to the present invention, preferably, the immunoreagent is used for labeling an immunofluorescent/immunohistochemical antibody or immunocolloid gold.

According to the present invention, preferably, a tumor area is labeled as $CK19^+$, a fibrosis area is labeled as $COL1A1^+$, macrophages are labeled as $CD68^+$, M2 macrophages are labeled as $CD206^+$, resident macrophages are labeled as $Lyve1^+$, T cells are labeled as $CD3^+CD8+$, proliferating cells are labeled as $Ki67^+$ and fibroblasts are labeled as $FAP^+$.

According to the present invention, preferably, the immunoreagent comprises a color developing agent labeled molecular probe specifically recognizing Cytokeratin 19, CD68, YAP1, FAP, COL1A1, p-PYK2, Lamin A/C, p-MLC2, Ki67, Lyve1, CD206, CD8 and CD3.

According to the present invention, preferably, the color developing agent labeled molecular probe specifically recognizing Cytokeratin 19, CD68, YAP1, FAP, COL1A1, p-PYK2, Lamin A/C, p-MLC2, Ki67, Lyve1, CD206, CD8 and CD3 comprises a primary antibody and secondary antibody, the primary antibody is a human monoclonal antibody specifically recognizing corresponding signal molecules, and the secondary antibody is a HistoFine secondary antibody meeting the resistance of the primary antibody.

3. An application of a PYK2 inhibitor in combination with a PD-1 inhibitor in preparation of a drug for treating pancreatic cancer is provided.

According to the present invention, the PYK2 inhibitor is capable of reducing an elastic modulus of cells or inhibiting differentiation of monocytes into macrophages.

According to the present invention, preferably, the PYK2 inhibitor comprises, but is not limited to, siRNA with Ptk2b as a target gene, sgRNA/CRISPR, a small molecule inhibitor and a Cre-loxP gene knock-out reagent with Ptk2b as a target gene.

According to the present invention, preferably, the siRNA with Ptk2b as the target gene is Si-Ptk2b_1: GGATCAT-CATGGAATTGTA (SEQID NO.1); Si-Ptk2b_2: GGACGAGGACTATTACAAA (SEQID NO.2); and Si-Ptk2b_3: CACATGAAGTCCGATGAGA (SEQID NO.3).

According to the present invention, preferably, the PYK2 inhibitor further comprises siRNA with piezo1 as a target gene, sgRNA/CRISPR, a small molecule inhibitor or a Cre-loxP gene knock-out reagent with piezo1 as a target gene.

According to the present invention, preferably, the siRNA with piezo1 as the target gene is Si-Piezo1_1: ATGGCCTCTGGGACCATGA (SEQID NO.4); Si-Piezo1_2: TCCGCCTACCAGATCCGCT (SEQID NO.5); and Si-Piezo1_3: GCCCTCTACCTGCGCAAGA (SEQID NO.6).

According to the present invention, preferably, the PD-1 inhibitor is an αPD-1 antibody.

The present invention has the beneficial effects that: aiming at the medical problems of pancreatic ductal adenocarcinoma, such as difficult diagnosis, difficult treatment and short five-year survival, the present invention finds a novel mechanical force signal checkpoint PYK2 (FIG. 1) for regulating and controlling the differentiation of the monocytes/macrophages by studying an interaction between the high-rigidity physical microenvironment of the pancreatic cancer and the immune cells. The monocytes/macrophages perceive a micro-environment physical signal through a mechanical force sensing receptor piezo1, in the high-rigidity physical microenvironment, the piezo1 is activated and $Ca^{2+}$ flows in, which leads to phosphorylation of PYK2 and assembly and activation of actomyosin, and further leads to nuclear transfer of YAP/TAZ, thus promoting expression of macrophage-related genes, and finally developing into mature macrophages. It is found by the inventor through research that, a number of mechanical force sensitive macrophages expressing $CD68^+p\text{-}PYK2^+YAP1^+$ in pancreatic cancer is obviously higher than that of an adjacent normal tissue, and the number of the macrophages is in positive correlation with a pancreatic cancer process, so that the mechanical force sensitive macrophages can be used as a pancreatic cancer diagnosis and prognosis index. An elasticity modulus of the cells can be reduced by inhibiting a mechanical force check point PYK2 of monocytes/macrophages, and differentiation of the monocytes into the macrophages is inhibited, so that a tumor micro-environment of the pancreatic cancer is improved. Growth of the pancreatic cancer can be remarkably inhibited through combined treatment, such as treatment of targeted inhibition of the mechanical force checkpoint PYK2 for regulating and controlling the differentiation of the monocytes/macrophages in combination with an immune checkpoint PD-1 blockade, and the lifetime of mice with the pancreatic cancer is remarkably prolonged. Therefore, a combined therapeutic schedule of the mechanical force check point PYK2 targeting the monocytes/macrophages in combination with immunotherapy, chemotherapy or radiotherapy has great application prospect and value in the treatment of the pancreatic cancer.

DESCRIPTION OF THE DRAWINGS

In order to make the objects, technical solutions and beneficial effects of the present invention clearer, the present invention provides the following drawings for description.

wherein, (A) shows a real object image of measurement of the elastic modulus of the pancreatic tissue by the nanoindenter, wherein the black arrow refers to a nanoindenter probe and the white arrow refers to the tissue; and (B) shows an average elastic modulus of the human pancreatic cancer tissue (n=7) and an adjacent normal tissue (n=3), wherein a P value is calculated by a t test.

Figure 3A:
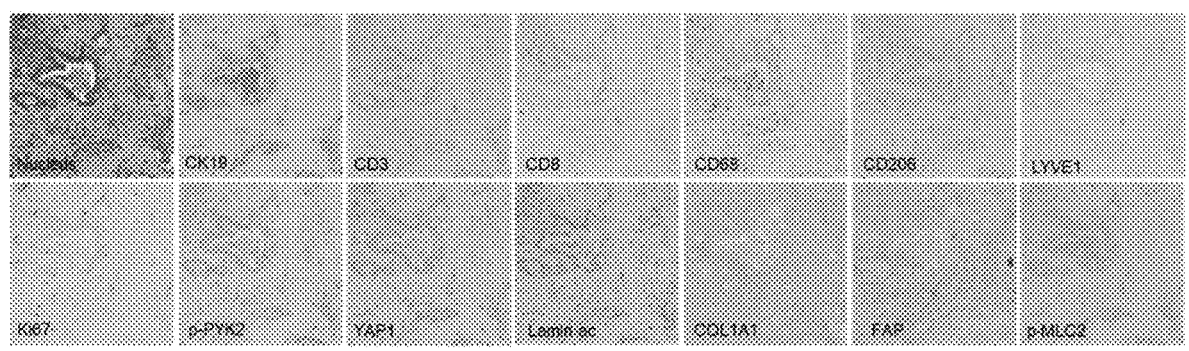
Figure 3B:
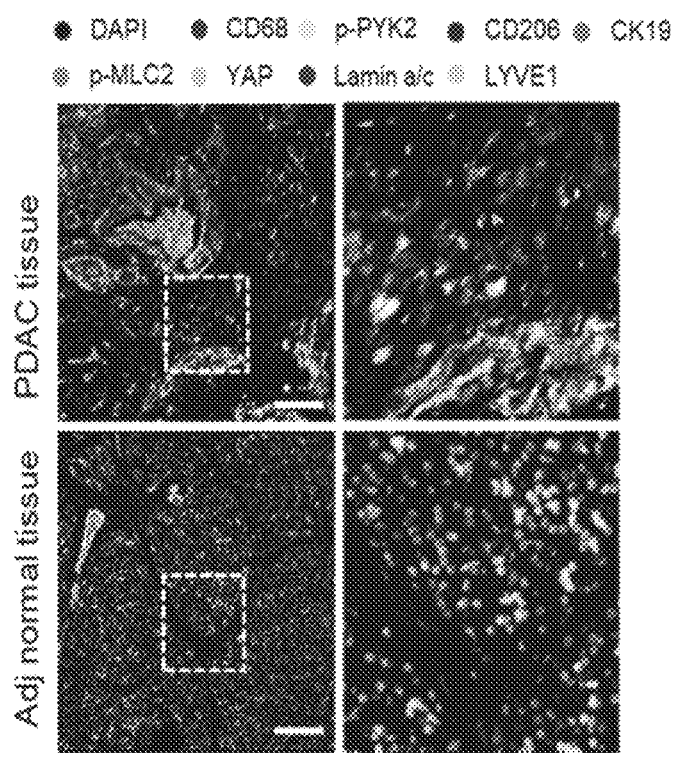
Figure 3B:
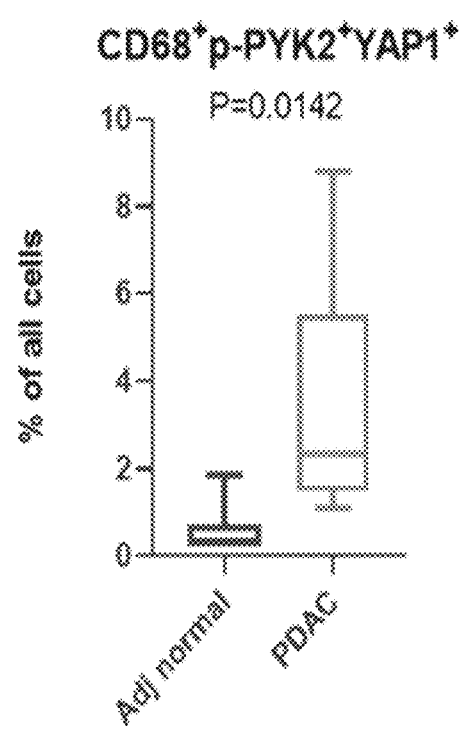
Figure 3C:
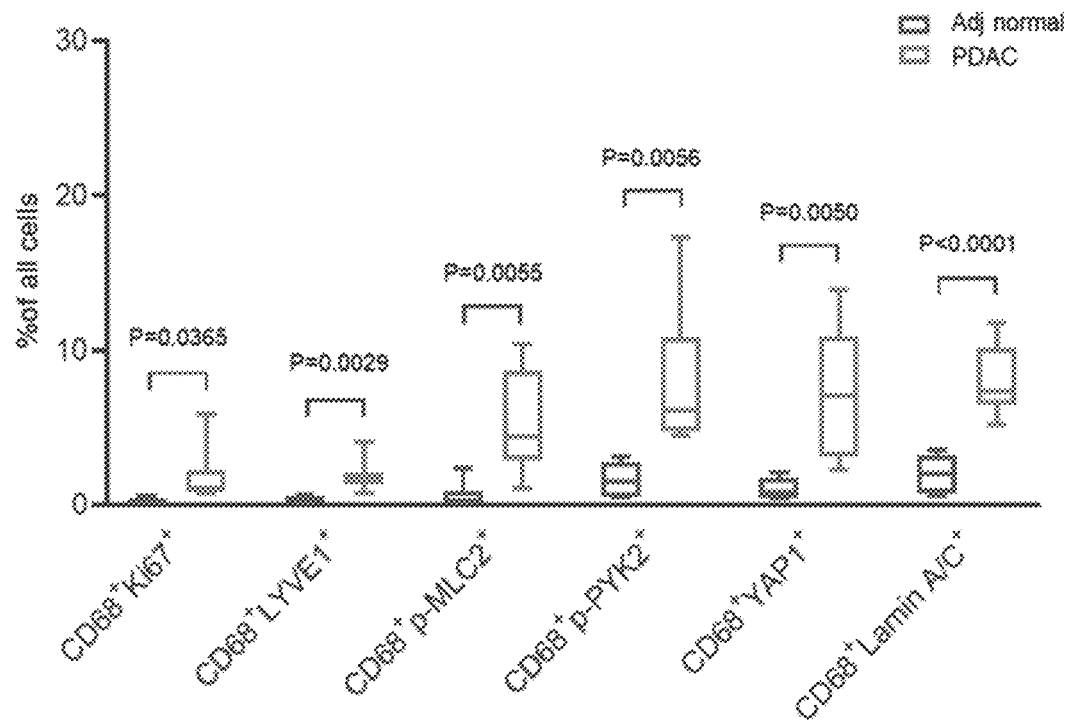
Figure 3D:
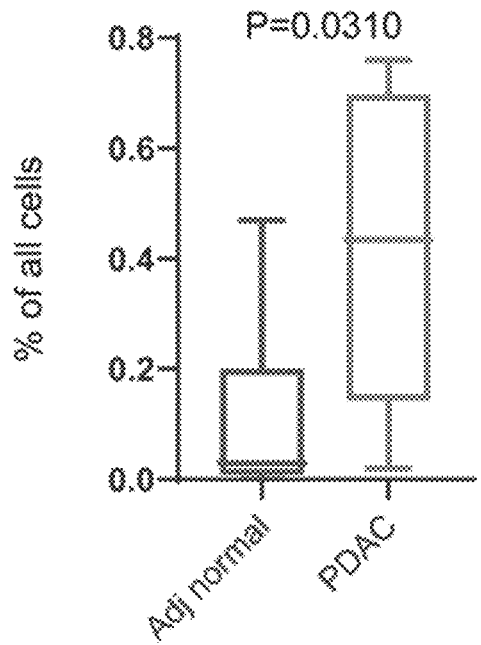

FIG. 3A, FIG. 3B, FIG. 3C and FIG. 3D show mIHC detection of the mechanical force sensitive monocytes/macrophages in human pancreatic cancer;

wherein, FIG. 3A shows mIHC staining images of human pancreatic cancer tissues; FIG. 3B shows mIHC staining fluorescence overlays of the pancreatic cancer tissues (n=8 ROIs) and the adjacent normal tissues (n=6 ROIs), and a statistical chart of p-PYK2$^+$YAP1$^+$ macrophages; and FIG. 3C shows a statistical chart of mechanical force signal expression of the monocytes/macrophages in the pancreatic cancer tissues (n=8 ROIs) and the adjacent normal tissues (n=6 ROIs), wherein a P value is calculated by a t test, and a scale is 200 μm.

Figure 4A:
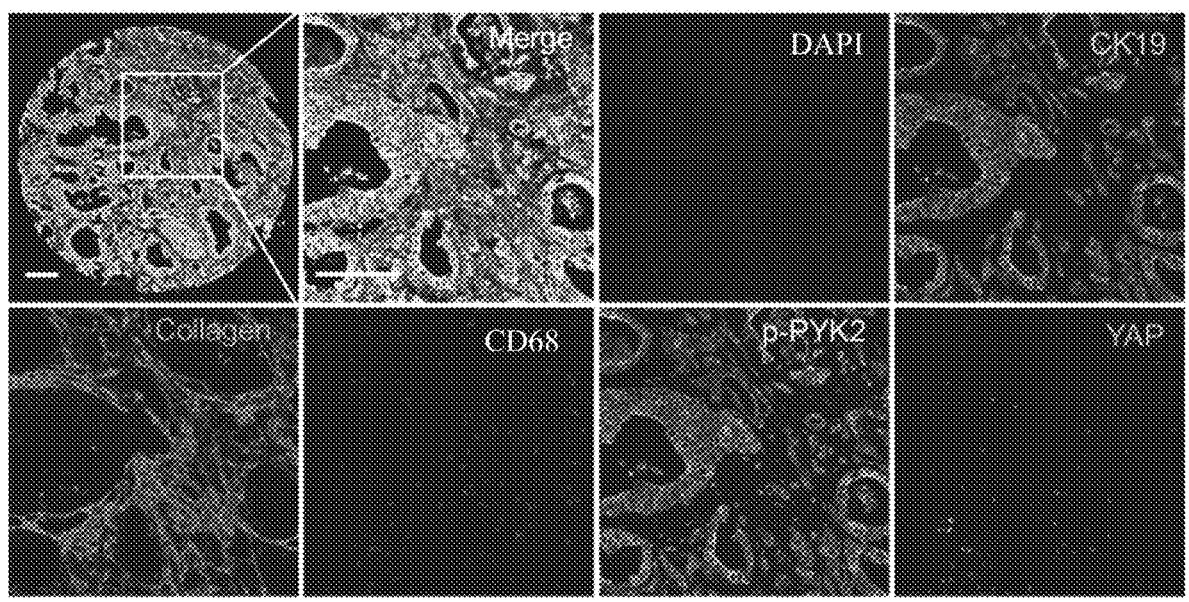
Figure 4B:
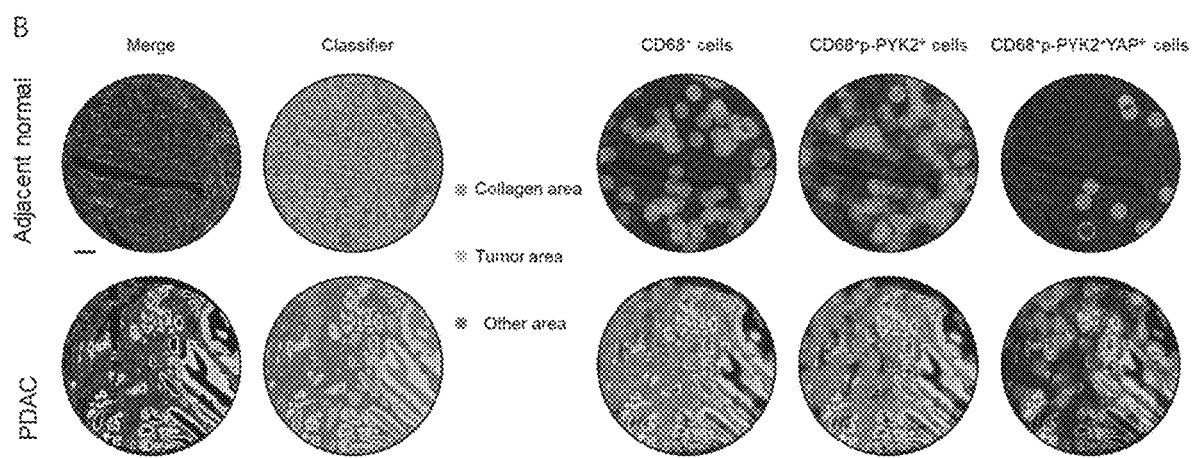
Figure 4C:
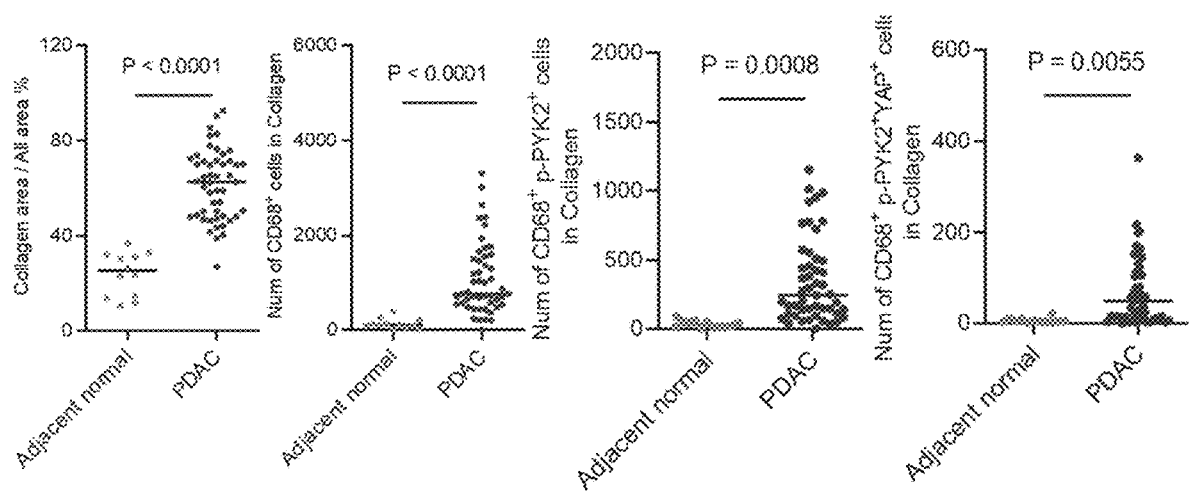
Figure 4D:
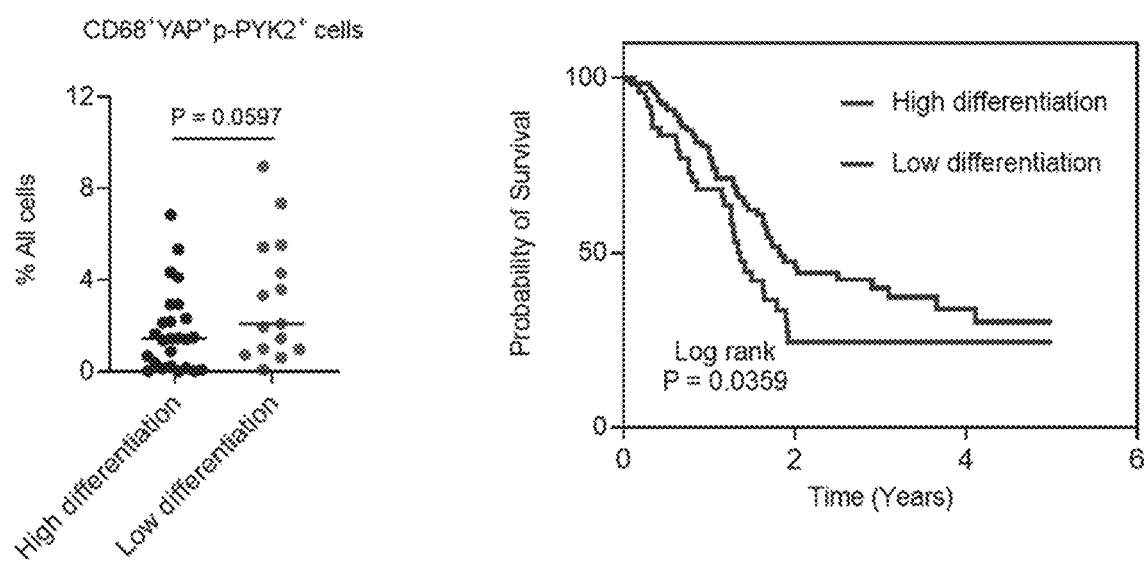

FIG. 4A, FIG. 4B, FIG. 4C and FIG. 4D show mIF detection of an application of the mechanical force sensitive monocytes/macrophages in pancreatic cancer diagnosis and pancreatic cancer prognosis evaluation;

wherein, FIG. 4A shows multiple immunofluorescence staining display images of CK19, CD68, p-PYK2, YAP and Collagen in TMA; FIG. 4B shows display images of collagen areas, tumor areas and other areas of the pancreatic cancer and the adjacent normal tissue in TMA; FIG. 4C shows a statistical chart of macrophages expressing p-PYK2 and YAP in the collagen areas of the pancreatic cancer tissues (n=49) and the adjacent normal tissues (n=12); and FIG. 4D shows expression of the macrophages expressing P-pyk2 and YAP in patients with high-differentiated (n=25) and low-differentiated (n=15) pancreatic cancers, and a correlation analysis chart between high expression and prognosis, wherein a P value is calculated by a t test, and a scale is 250 μm.

Figure 5A:
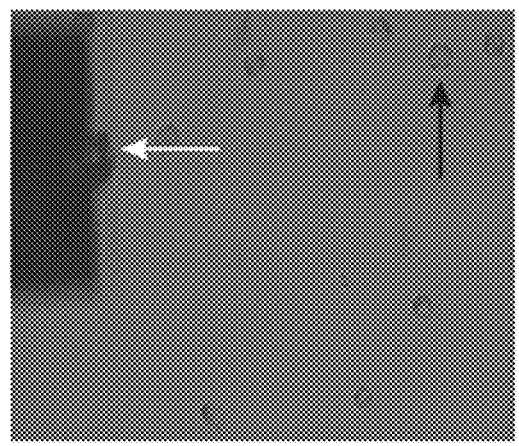
Figure 5B:
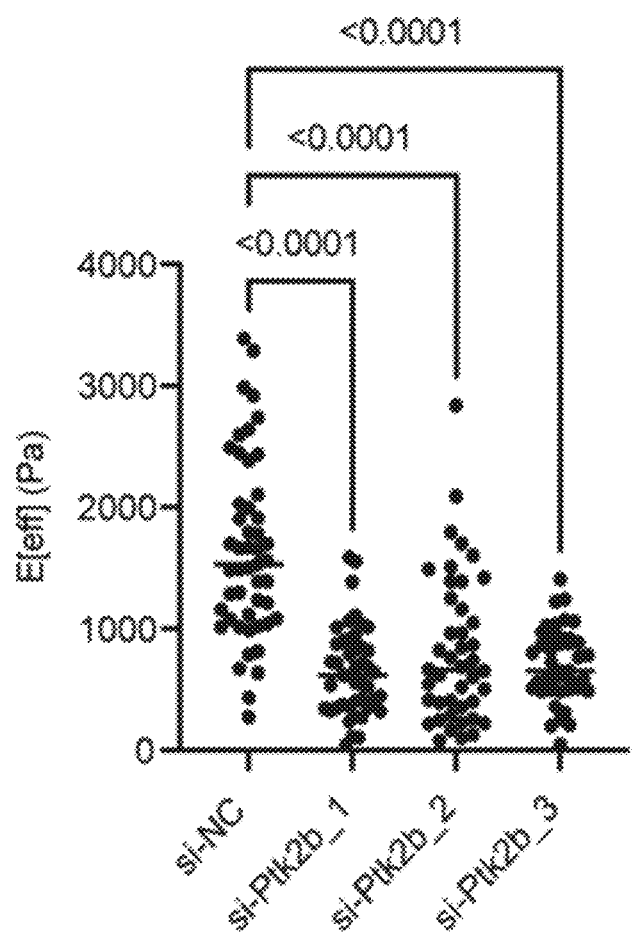
Figure 5C:
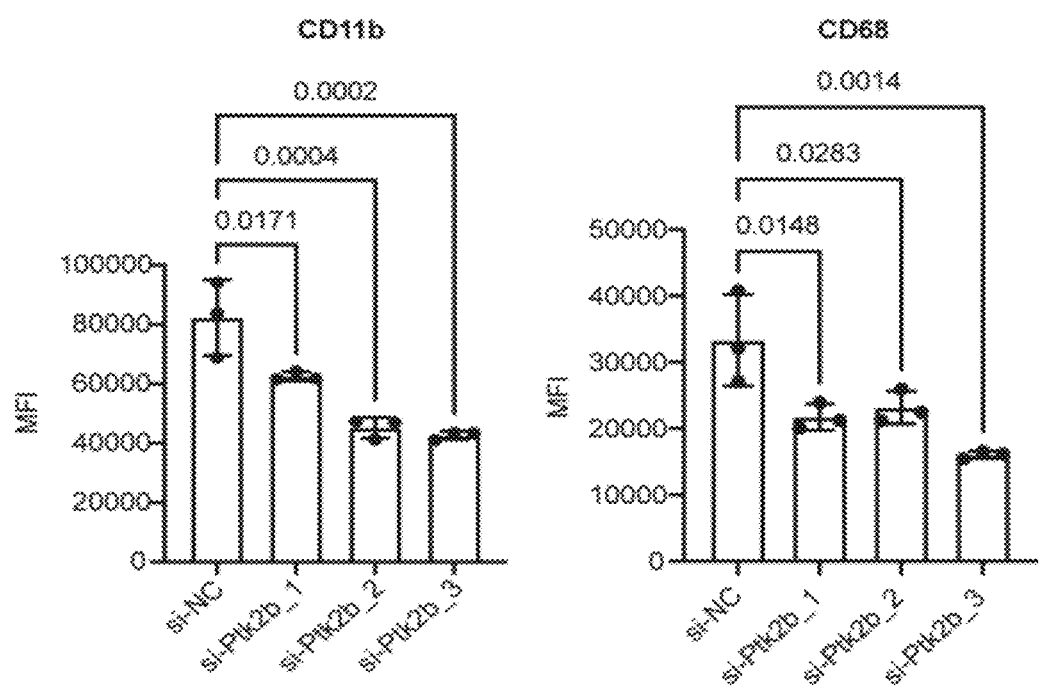

FIG. 5A, FIG. 5B and FIG. 5C show an application of suppression of Ptk2b by siRNAs in inhibiting differentiation of human monocytes into macrophages;

wherein, FIG. 5A shows a real object image of detection of a cellular elastic modulus by a nanoindenter, wherein the white arrow refers to a nanoindenter probe and the black arrow refers to a THP-1 cell; FIG. 5B shows an influence of the suppression of Ptk2b by siRNAs on the elastic modulus of the THP-1 cells, wherein in the case of si-NC, n=50; in the case of si-Ptk2b_1, n=45; in the case of si-Ptk2b_2, n=43; and in the case of si-Ptk2b_3, n=41; and FIG. 5C shows flow cytometry analysis of an influence of the suppression of Ptk2b by siRNAs on CD11b and CD68 after the THP-1 cells are differentiated into the macrophages, n=3, wherein a P value is calculated by one-way ANOVA.

Figure 6:
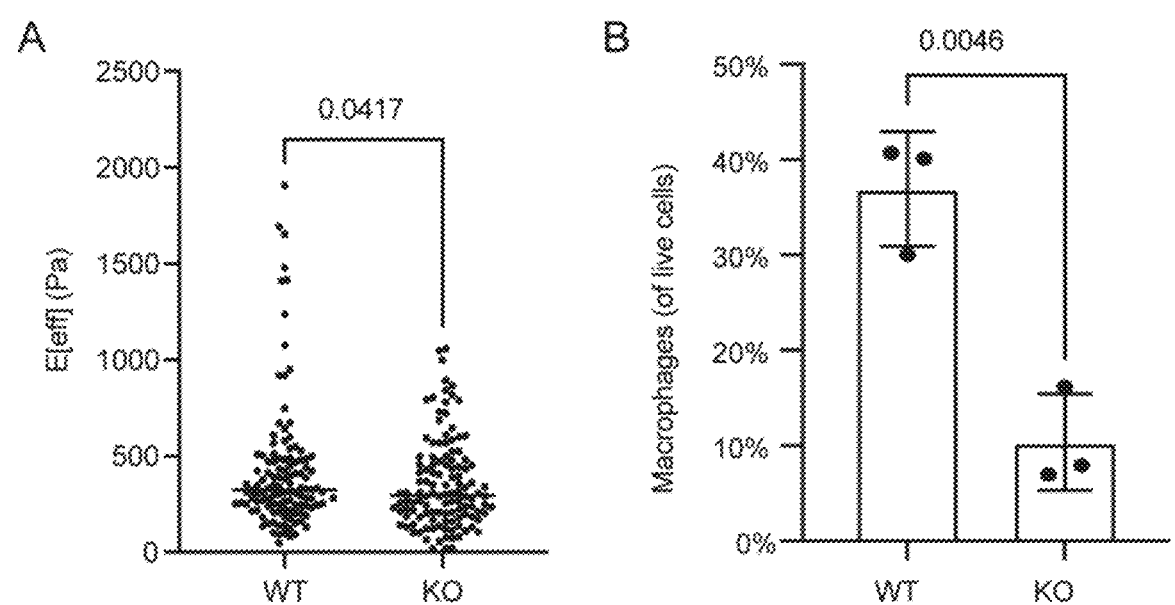

FIG. 6 shows an application of the knockout of Ptk2b gene in inhibiting differentiation of mouse monocytes into macrophages;

wherein, (A) shows a cellular elastic modulus of macrophages derived from mouse bone marrow with normal expression and knockout of Ptk2b, wherein in the case of WT, n=118; and in the case of KO, n=120; and (B) shows flow cytometry analysis of proportion statistics of the mouse bone marrow-derived cells differentiated into the macrophages with normal expression and knockout of Ptk2b, n=3, in which WT refers to normal gene expression; and KO refers to gene knockout, wherein a P value is calculated by a t test.

Figure 7A:
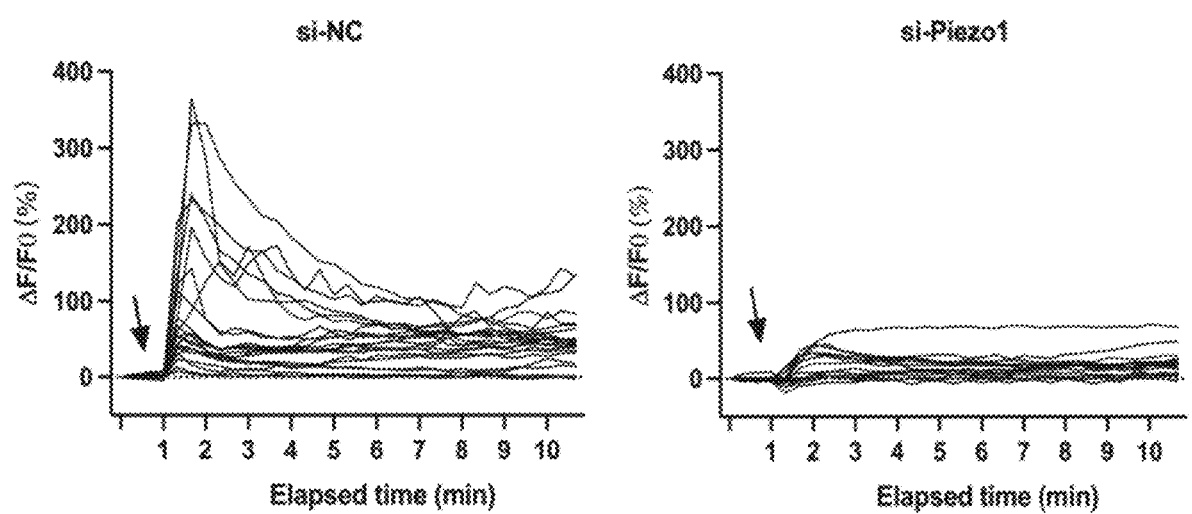
Figure 7B:
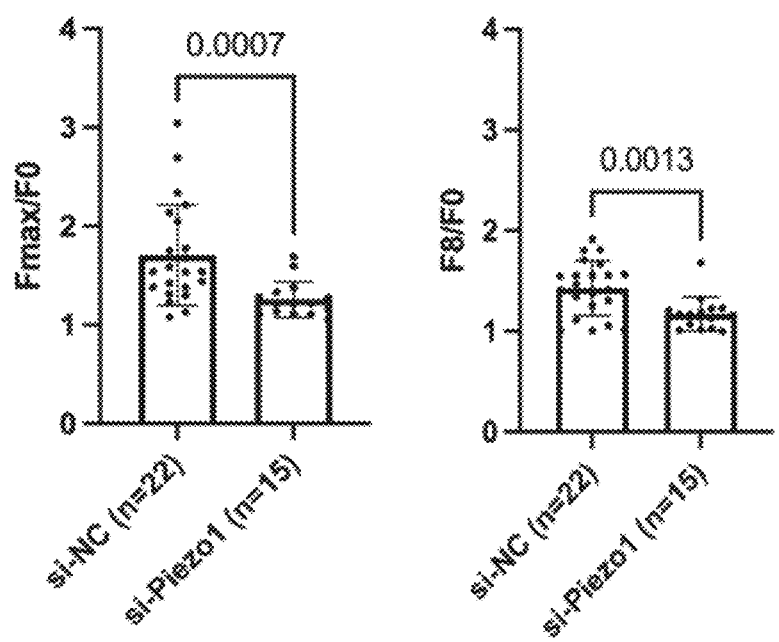
Figure 7C:
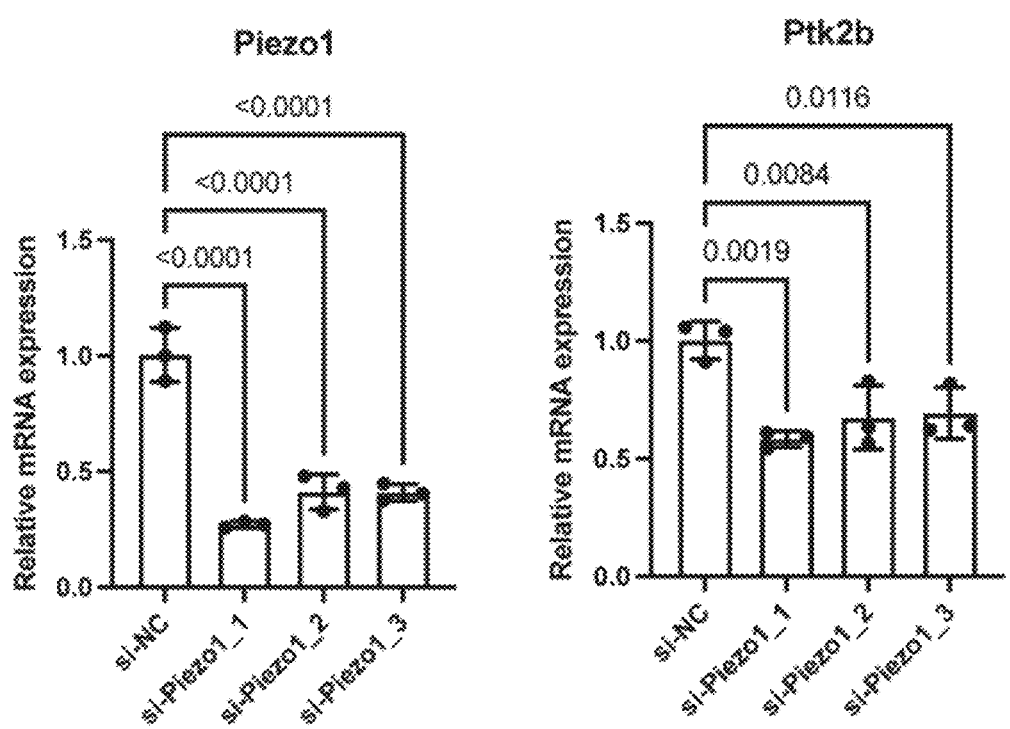
Figure 7D:

FIG. 7A, FIG. 7B, FIG. 7C and FIG. 7D show a function of a mechanical force sensing receptor Piezo1 in regulating and controlling a novel mechanical force signal check point PYK2;

wherein, FIG. 7A shows an influence of the Piezo1 inhibitor on inflow of calcium ions in THP-1 cells, wherein the arrow refers to a time point of adding Yoda1, in the case of si-NC, n=22; and in the case of si-Piezo1, n=15; FIG. 7B shows a ratio of a calcium ion signal fluorescence peak value and a calcium ion signal stabilization (8 minutes) fluorescence value of the THP-1 cells after adding Yoda1 to a calcium ion fluorescence value before adding Yoda1, wherein a P value is calculated by a t test; FIG. 7C shows an influence of the Piezo1 inhibitor on mRNA expression of Piezo1 and Ptk2b in the THP-1 cells, wherein a P value is calculated by one-way ANOVA; and FIG. 7D shows an influence of the Piezo1 inhibitor on protein expression and phosphorylation of Ptk2b in the THP-1 cells.

Figure 8:
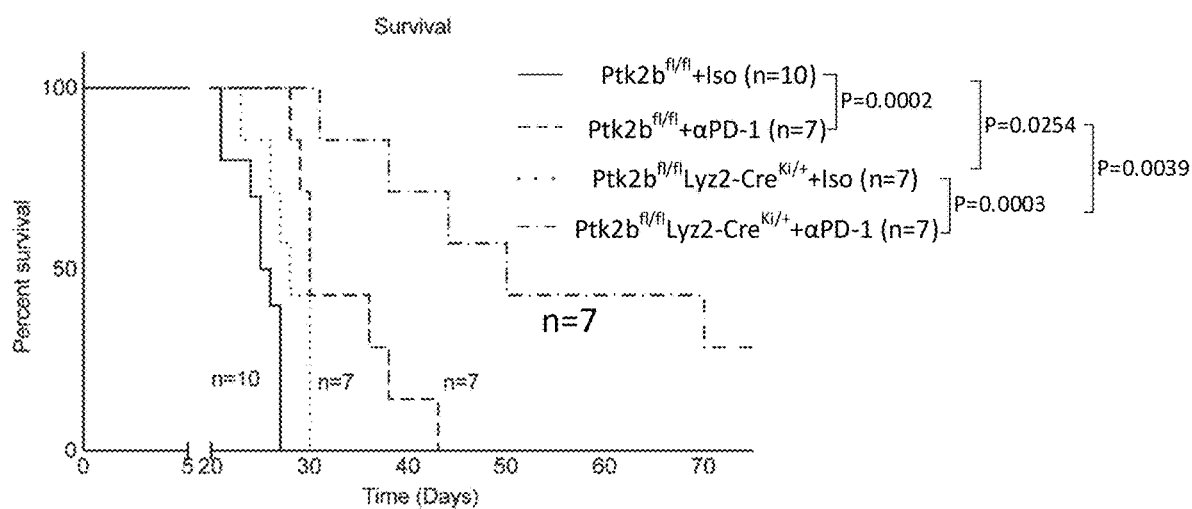

FIG. 8 shows an application of a combined therapeutic schedule of the mechanical force checkpoint PYK2 of the monocytes/macrophages in combination with an immune checkpoint PD-1 in treatment of the pancreatic cancer (in the case of Ptk2b$^{fl/fl}$+Iso, n=10; in the case of Ptk2b$^{fl/fl}$+PD-1, n=7; in the case of Ptk2b$^{fl/fl}$Lyz2-Cre$^{ki/+}$+Iso, n=7; and in the case of Ptk2b$^{fl/fl}$Lyz2-Cre$^{ki/+}$+αPD-1, n=7; and a P value is calculated by Gehan-Breslow-Wilcoxon detection).

DETAILED DESCRIPTION OF PREFERRED EMBODIMENTS

The present invention is further described hereinafter with reference to the drawings and specific embodiments, so that those skilled in the art can better understand and implement the present invention. However, the mentioned embodiments should not be taken as a limitation of the present invention.

Embodiment 1

A Method for Measuring an Elastic Modulus of a Pancreatic Cancer Tissue was Provided, which Comprised Specific Steps as Follows.

1) Samples of a tumor tissue and an adjacent normal tissue from a pancreatic cancer patient were taken respectively, and transported to a laboratory by using cold PBS. The tissues were cut into a size with a length of about 1 cm and a thickness of about 0.5 cm by using a surgical blade, adhered to a bottom of a culture dish with biological tissue glue (Pattex, Henkel Adhesives Company Limited), and added with a PBS buffer solution to immerse the tissues, as shown in FIG. 2A.

2) A nanoindenter probe (0.5 N/m) was connected to a nanoindenter (Optics11 life, Amsterdam, The Netherlands), the tissues were calibrated by using a confocal dish (Cat. No. 801002, NEST), and then elastic moduli of the tissues were measured. Parameters were specifically set as follows: a downward pressing process lasted for 2 seconds, and a downward pressing depth was 10000 nm; the downward pressing was maintained for 1 second; and a lifting process lasted for 2 seconds. The elastic moduli were calculated by software Dataviewer version 2.2 (Piuma; Optics11, Amsterdam, The Netherlands).

Figure 1:
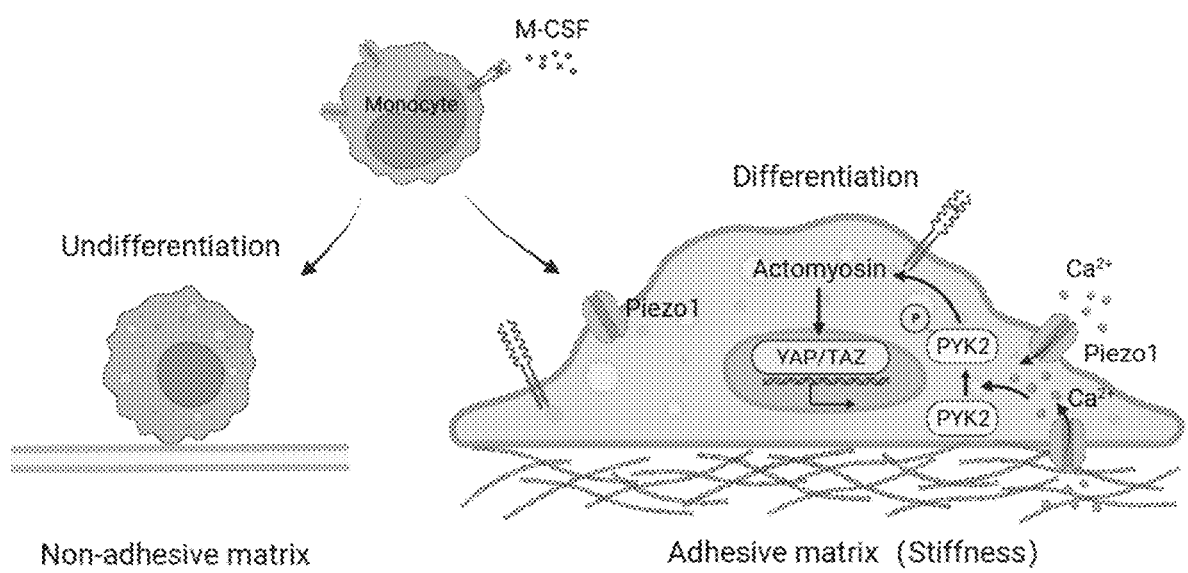
FIG. 1 shows a mechanical force signal pathway in which a mechanical force check point PYK2 participates in regulating and controlling differentiation of monocytes/macrophages.
Figure 2:
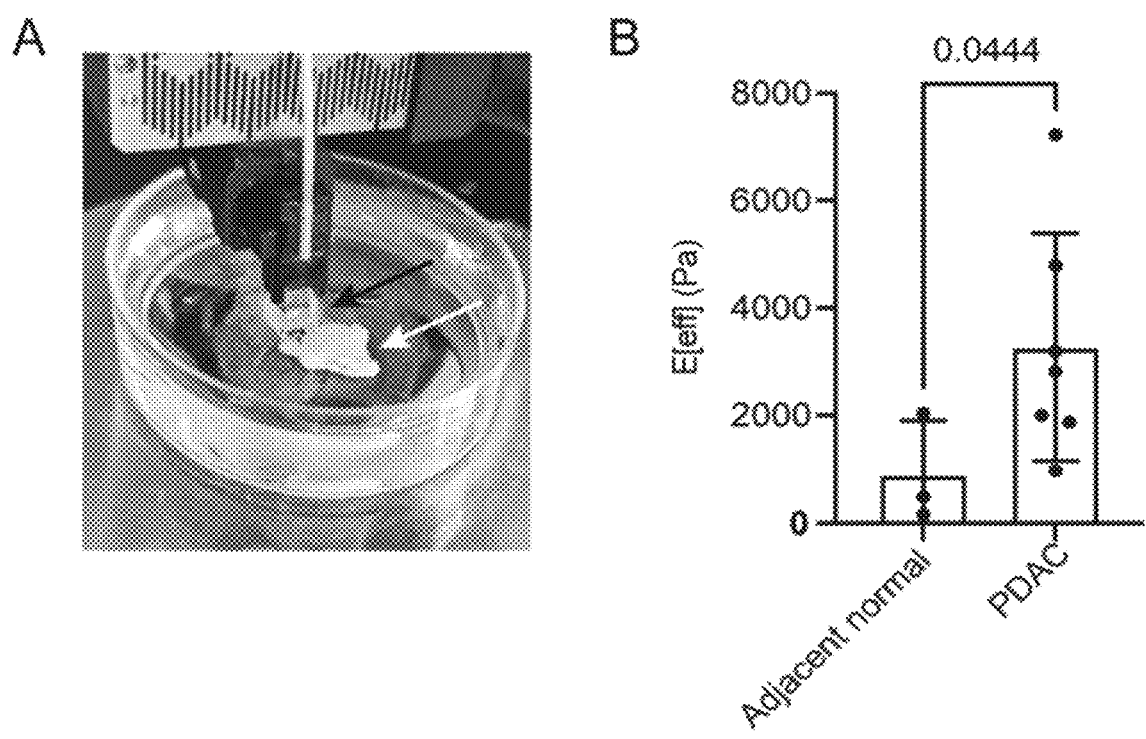
FIG. 2 shows an elastic modulus of a human pancreatic cancer tissue measured by a nanoindenter.

Results were shown in FIG. 2B, and the elastic modulus of the pancreatic cancer tissue was significantly higher than that of the adjacent normal tissue. Therefore, this method could be used for detecting the pancreatic cancer tissue and the adjacent normal tissue.

Embodiment 2

A Method for Detecting Activation of Mechanical Force Signal Pathway of Monocytes/Macrophages in Pancreatic Cancer was Provided, which Comprised Specific Experimental Steps as Follows.

1) The obtained human pancreatic cancer tissue and adjacent normal tissue were embedded with paraffin, cut into 5 mm paraffin sections, and dried at 65° C. for 1 hour until the paraffin was completely melted. Slides were subjected to gradient treatment with xylene twice, 5 minutes each time; subjected to treatment with 100% ethanol and 95% ethanol twice, 2 minutes each time; subjected to treatment with 70% ethanol once, 2 minutes each time; subjected to treatment with deionized water twice, 2 minutes each time; and subjected to staining with hematoxylin (Cat. No. CS700, Dako) for 1 minute, rinsed with deionized water twice, and then washed in TBST for 2 minutes. The tissues were sealed with a sealing agent (VectaMount AQ Aqueous Mounting, Cat. No. LS-J1038-60, Vector lab), and images were collected with a pathological section scanner.

2) After scanning, the sections were stored in TBST (which could be allowed to stand overnight herein), and shaken and washed in TBST for 1 minute. Cover slips were removed gently, and the tissues were blocked with peroxidase (245 mL methanol+30% 5 mL hydrogen peroxide), incubated at room temperature for 30 minutes, and washed in TBST for 1 minute. The slides were placed in an antigen retrieval solution (Cat. No. GT100411, GeneTack), and the retrieval solution was boiled in a microwave oven, heated with maximum fire for 30 seconds, heated with completely high fire for 3 minutes, heated with low fire for 12 minutes in a half-covered state, allowed to stand at room temperature for about 15 minutes for cooling, and treated with deionized water and TBST for 1 minute respectively.

3) The TBST around the tissues was wipe-dried. Each slide was dropwise added with 100 μL of antigen blocking solution (2 mL 5% goat serum+38 mL PBS+1 g BSA) and blocked at room temperature for 10 minutes, then the blocking solution was removed, and a back surface of the slide and a periphery of the tissue were wipe-dried. Each slide was incubated with 100 μL of CD8 primary antibody diluent (1:100; Cat. No.853365, CST) at room temperature for 1 hour, and washed with TBST for three times after incubation, 2 minutes each time; added with HistoFine secondary antibody (Vector, Mouse/Rabbit) according to the resistance of the primary antibody to incubate for 30 minutes; and then added with an AEC color-developing solution (Cat. No. SK-4200, Vector lab, 10 mL ddH$_2$O+1st Reagent 4 Drops+2st Reagent 6 Drops+3st Reagent 4 Drops) prepared, and wrapped with a tin foil to store in the dark at 4° C.

4) After incubation, the slides were shaken and washed with TBST for three times, 2 minutes each time, and then transferred into deionized water for simple cleaning. Each slide was dropwise added with 100 μL of AEC color-developing solution and incubated at room temperature for 15 minutes. Color-developing conditions of the slides were observed under a microscope, and after confirming staining effects, the slides were washed with TBST, sealed with a sealing agent and then scanned. After scanning, the slides were soaked in TBST overnight, cover slips falling off by themselves were removed gently, and then the slides were rinsed in deionized water and 70% alcohol for 1 minute.

5) The steps 2) to 4) were repeated for cyclic staining. In this experiment, mIHC staining had a total of 15 cycles, comprising 13 biological staining markers (Cycle 2 to Cycle 16) except for a white section serving as a negative control (Cycle 15) and hematoxylin serving as nuclear staining (Cycle 1), which contained and represented various cellular mechanical force signal proteins, immune cells and fibroblasts. Specific staining sequence and antibody information were shown in the following table:

TABLE 1

| Cyclic sequence of mIHC staining and antibody information | | | | | |
| --- | --- | --- | --- | --- | --- |
| | Cycle 1 | Cycle 2 | Cycle 3 | Cycle 4 | Cycle 5 |
| Primary Ab | Hematoxylin | CD8 | Cytokeratin 19 | p-MLC2 | Lamin A/C |
| Clone/Product # | N/A | 85336S | ab52625 | 3671S | ab 133256 |
| Vendor | Dako | CST | Abcam | CST | Abcam |
| Concentration | N/A | 1:100 | 1:600 | 1:200 | 1:300 |
| Reaction | N/A | 60 min | 60 min | 60 min | 60 min |
| Secondary Ab | N/A | Mouse | Rabbit | Rabbit | Rabbit |
| AEC reaction | N/A | 15 min | 6 min | 20 min | 5 min |
| | Cycle 6 | Cycle 7 | Cycle 8 | Cycle 9 | Cycle 10 |
| Primary Ab | CD3 | YAP1 | CD206 | p-PYK2 | COL1A1 |
| Clone/Product # | ab16669 | ac52771 | 91992S | ab4800 | 72026S |
| Vendor | Abcam | Abcam | CST | Abcam | CST |
| Concentration | 1:200 | 1:80 | 1:500 | 1:200 | 1:200 |
| Reaction | 60 min | 60 min | 60 min | 60 min | 60 min |
| Secondary Ab | Rabbit | Rabbit | Rabbit | Rabbit | Rabbit |
| AEC reaction | 6 min | 20 min | 7 min | 25 min | 20 min |

TABLE 1-continued

Cyclic sequence of mIHC staining and antibody information

| | Cycle 11 | Cycle 12 | Cycle 13 | Cycle 14 | Cycle 15 |
|---|---|---|---|---|---|
| Primary Ab | CD68 | FAP | Ki67 | LYVE1 | Negative Control |
| Clone/Product # | ab955 | 66562S | ab16667 | ab219556 | N/A |
| Vendor | Abcam | CST | Abcam | Abcam | N/A |
| Concentration | 1:5000 | 1:100 | 1:200 | 1:10000 | N/A |
| Reaction | 60 min | 60 min | 60 min | 60 min | N/A |
| Secondary Ab | Rabbit | Rabbit | Rabbit | Rabbit | N/A |
| AEC reaction | 15 min | 10 min | 10 min | 10 min | N/A |

6) After staining, the collected images were subjected to quantitative analysis and fluorescent coloring by using ImageScopex 64 (Aperio Technologies), Cell profiler (Broad Institute) and FSC Express 7 Research Edition (Win64) (De Novo Software).

Results were shown in FIG. 3A, FIG. 3B, FIG. 3C and FIG. 3D, and a collagen$^+$ area of the pancreatic cancer tissue (corresponding to COL1A1 in FIG. 3A) was significantly higher than that of the adjacent normal tissue, which proved that the pancreatic cancer had the characteristics of high fibrosis and corresponded to a high-rigidity physical microenvironment of the pancreatic cancer. CD68$^+$p-PYK2$^+$YAP1$^+$ cells in the pancreatic cancer tissue were significantly increased (FIG. 3B), which indicated the high infiltration of such macrophages in human pancreatic cancer. According to spatial location analysis, the macrophages were mostly located in a fibrosis area, and positive co-expression of CD68$^+$ cells and mechanical force signal markers p-PYK2, YAP1, p-MLC2 and Lamin A/C was significantly up-regulated, as shown in FIG. 3C, which indicated that a mechanical force signal of the macrophages in the human pancreatic cancer tissue was highly activated.

Embodiment 3

A Method for Detecting Mechanical Force Sensitive Monocytes/Macrophages and an Application Thereof in Pancreatic Cancer Diagnosis and Prognosis were Provided, and the Method Comprised Specific Steps as Follows.

1) A tissue slide of TMA (Shanghai Outdo Biotech Co., Ltd.) of a pancreatic cancer patient was baked at 65° C. for 2 hours and then soaked in xylene for 10 minutes, which was repeated for 3 times. The slide was subjected to gradient ethanol soaking: at 100% for 5 minutes; 95% for 5 minutes; and 70% for 5 minutes, and rinsed with ddH$_2$O for 3 minutes. An antigen retrieval solution (Cat. No. GT100411, GeneTack) was boiled in a microwave oven with high fire, and then the slide was put into an antigen retrieval box, retrieved in the microwave oven with low fire for 20 minutes, and naturally cooled at room temperature for 15 minutes. The slide was rinsed with ddH$_2$O, and then the sample was treated with 3% H$_2$O$_2$ (Cat. No. STBH9407, Sigma) for 10 minutes to remove endogenous peroxidase, and washed with TBST for 3 minutes.

2) After washing with TBST, the TBST buffer solution was removed from the section, an area of the tissue sample on the slide was circled with an immunohistochemical pen, and the tissue was stained by using an Opal kit (Cat. No. NEL811001KT, Opal 6-Plex Manual Detection Kit, Akoya biosciences). A blocking buffer was dropwise added to cover the area of the tissue, and the tissue was incubated under moisture retention for 10 minutes. After incubation, the blocking buffer on the slide was removed, and each tissue was dropwise added with about 100 µL of CD68 primary antibody (1:300; Cat. No. ab955, Abcam), incubated at room temperature for 1 hour under moisture retention, and shaken and rinsed with TBST at room temperature for 3 times.

3) After rinsing, the slide was dropwise added with an HRP secondary antibody to immerse the area of the tissue, incubated at room temperature under moisture retention for 10 minutes, rinsed with TBST, and shaken at room temperature for 3 times. After removing TBST, 1×TSA color-developing solution (1:150; Opal 690) was dropwise added to immerse the area of the tissue, and the slide was incubated at room temperature under moisture retention for 10 minutes, and shaken and rinsed with TBST at room temperature for 3 times. The slide was subject to microwave treatment to remove the primary antibody and the secondary antibody with high fire for 3 minutes and with low fire for 20 minutes, and then naturally cooled at room temperature, and the slide was rinsed with ddH$_2$O.

4) YAP (1:200; Cat. No. ab52771, Abcam), CK19 (1:500; Cat. No. MA5-11458, Invitrogen), COL1A1 (1:200; Cat. No. 72026t, CST) and p-PYK2 (1:100; Cat. No. ab4800, Abcam) indexes were re-stained, and the steps 1) to 3) were repeated until all antigens were labeled. The retrieved and washed slide was dropwise added with a DAPI (1:500; Cat. No. M5107, AbMole) working solution, and incubated under moisture retention for 5 minutes. An anti-fluorescence quenching sealing agent was dropwise added on the slide for slide sealing. Images were collected by a Vectra multi-spectral imaging system and subjected to quantitative statistical analysis by using HALO (Indica Labs), and analysis was carried out in combination with prognosis information of a patient in TMA.

Results were shown in FIG. 4A, and expressions of CD68, COL1A1, p-PYK2 and YAPI of the pancreatic cancer tissue were significantly higher than those of the adjacent normal tissue. FIG. 4B and FIG. 4C showed that expression of CD68 in and around the Collagen area was increased, and mechanical force signals p-PYK2, YAP1 and p-MLC2 were significantly activated. FIG. 4D showed that expression of macrophages with mechanical force response, which were a CD68$^+$p-PYK2$^+$YAP1$^+$ cell mass, was increased in a patient with poorly differentiated cancer, and the poorly differentiated cancer with high expression of the CD68$^+$p-PYK2$^+$YAP1$^+$ cell mass was significantly related to poor prognosis of a pancreatic cancer patient. Therefore, the CD68$^+$p-PYK2$^+$YAP1$^+$ cells could be used as a diagnostic index of the pancreatic cancer, and could be used for evaluating the prognosis of the pancreatic cancer patient.

Embodiment 4

A Novel Mechanical Force Signal Checkpoint PYK2 and an Application Thereof in Regulating and Controlling Differentiation of Human Monocytes into Macrophages were Provided.

The present invention provided the following three siRNAs targeting human Ptk2b gene: Si-Ptk2b_1: GGATCATCATGGAATTGTA (SEQID NO. 1); Si-Ptk2b_2: GGACGAGGACTATTACAAA (SEQID NO. 2); Si-Ptk2b_3: CACATGAAGTCCGATGAGA (SEQID NO. 3, and functions of the gene inhibitors in differentiation of the monocytes into the macrophages under a mechanical force of a monocyte-induced micro-environment were verified, by specific steps as follows.

1) Transfection of THP-1 cells: the cells were inoculated into a 24-well plate at a density of 2.5×105/ well. A transfection reagent was prepared: A: 50 μL of low serum culture medium (Opti-MEM I Reduced Serum Medium, Cat. No. 31985070, Gibco) was added with 3 μL of transfection reagent (Lipofectamine™ RNAiMAX Transfection Reagent, Cat. No. 13778075, Invitrogen). B: 50 μL of low serum culture medium (Opti-MEM I Reduced Serum Medium, Cat. No. 31985070, Gibco) was added with 1 μL of siRNA (RIBO BIO). A and B were mixed and incubated at room temperature for 5 minutes, and 50 μL of the mixture was added with the THP-1 cells to culture overnight.

2) A cell suspension was collected and centrifuged at 1000 rpm and room temperature for 5 minutes, a supernatant was removed, and PMA (50 ng/ml, Cat. No. p1585, Sigma) was added to induce for 24 hours.

3) The cell culture medium was replaced by PBS, an instrument was calibrated by using a confocal dish, and then an elastic modulus of the cells was measured. Results were shown in FIG. 5A, and compared with a control group of si-NC, si-Ptk2b_1, si-Ptk2b_2 and si-Ptk2b_3 could significantly reduce the elastic modulus of the THP-1 macrophages.

4) The cells were collected, centrifuged, washed with PBS once, then added with 1 μL of Fixable Viability Stain 780 (Cat No. 565388, BD), mixed evenly, incubated on ice for 20 minutes, and washed with an FACS Buffer (2% BSA in PBS) twice. The solution was added with 2.5 μL of FC blocking antibody (Cat. No. 422302, Biolegend), blocked on ice for 20 minutes, then added with 2.5 μL of CD14-BV421 (Cat. No. 563743, BD) antibody and 1 μL of CD11b-PE (Cat. No. 101207, Biolegend) antibody, incubated on ice in the dark for 20 minutes, and then washed with an FACS Buffer twice. The solution was added with 100 μL of cell fixing solution (Cat. No. 00-8222-49, eBioscience), incubated at room temperature in the dark for 40 minutes, and then washed with a prepared membrane permeation solution (Cat. No. 00-8333-56, eBioscience) twice. The cells were resuspended to 100 μL of membrane permeation solution, added with 1.5 μL of CD68-AF647 (Cat. No. 333820, Biolegend), incubated on ice in the dark for 20 minutes, then washed with the membrane permeation solution twice, resuspended to 100 μL of FACS buffer, and detected on a computer. Results were shown in FIG. 5B, and PYK2 inhibitors si-Ptk2b_1, si-Ptk2b_2 and si-Ptk2b_3 could significantly inhibit fluorescence intensities of CD11b and CD68 of the THP-1 cells, which proved that the differentiation of the THP-1 monocytes into the macrophages could be significantly inhibited by inhibiting PYK2.

Embodiment 5

A Novel Mechanical Force Signal Checkpoint PYK2 and an Application Thereof in Regulating and Controlling Differentiation of Mouse Monocytes into Macrophages were Provided.

1) A piranha solution (30 mL 30% $H_2O_2$ and 70 mL $H_2SO_4$) was prepared, and a cover slip with a diameter of 30 mm was placed in the piranha solution for 3 hours, then washed with deionized water until it was neutral, and ultrasonically washed with ethanol twice, 5 minutes each time. A reaction solution was prepared: 3 mL of 10% acetic acid and 1 mL of 3-(methacryloyloxy)propyl trimethoxysilane were added into 100 mL of ethanol. The cover slip was placed into the reaction solution to react at 80° C. for 5 hours, then ultrasonically washed with ethanol for 3 times, and then hermetically stored in a refrigerator at 4° C.

2) GelMA was prepared: 5 g of gelatin (Cat No.9382, Sigma) was dissolved in 50 mL of PBS, and 1 mL of methacrylic anhydride was dropwise added into the gelatin solution while stirring at 50° C. to react for 2 hours. 100 mL of PBS at 40° C. was added to terminate the reaction. The mixture was dialyzed by using a 12-14 kDa dialysis bag at 40° C. for 4 days. The mixture was freeze-dried to remove water, and stored in a refrigerator at 4° C.

3) A GelMA solution with a mass fraction of 8% was prepared by PBS and dissolved at 37° C. A PEG (Cat. No. 455008, Sigma) solution with a mass fraction of 20% was prepared by PBS, and dissolved by vortex oscillation. 20 mg/mL LAP (Cat. No. 900889, Sigma) solution was prepared by PBS, ultrasonically dissolved for 30 seconds, and stored on ice in the dark, which was prepared for current use. The GelMA solution and the PEG solution were mixed evenly according to a volume ratio of 1:1. LAP was added to allow a mass ratio of the LAP to hydrogel to be 1:100, and oscillated by a vortex mixer for 20 seconds. The mixture of the three was dropwise added on an anti-sticking board, covered with a treated cover slip, and irradiated with an ultraviolet lamp at 365 nm for 2 minutes for chemical cross-linking. An elastic modulus of the hydrogel measured by a rheometer was about 10 kPa. The prepared hydrogel was transferred into a 6-well plate, irradiated with an ultraviolet lamp for 10 minutes for sterilization and disinfection, and washed with PBS twice for later use.

4) Mouse bone marrow-derived cells with Ptk2b gene expression and gene knockout were respectively added into M-CSF (20 ng/ml, Cat No. 315-02, Peprotech), and the cells were inoculated into the hydrogel according to a density of $2×10^6$ cells, and cultured in a CO2 incubator with a volume fraction of 5% at 37° C. for 6 days to differentiate into the macrophages.

5) After 6 days of differentiation, the cell culture medium was replaced by PBS. A nanoindenter probe was connected to a nanoindenter (Optics11 life, Amsterdam, The Netherlands), the cells were calibrated by using a confocal dish, and then an elastic modulus of the cells was measured. Results were shown in FIG. 6A, and after PYK2 protein expression was inhibited, an elastic modulus of the mouse macrophages was significantly reduced.

6) After 6 days of differentiation, supernatant cells and adherent cells were collected, wherein the adherent cells were scraped off gently with a palette knife. The cells were centrifuged, then washed with PBS once, then added with 1 μL of Fixable Viability Stain 700 (Cat No. 564997, BD), mixed evenly, incubated on ice for 20 minutes, and washed with an FACS Buffer twice. The solution was added with 2 μL of FC blocking antibody (Cat. No. 156604, Biolegend), blocked on ice for 20 minutes, then added with 1 μL of CD45-BV510 (Cat No.563891, BD) antibody, 0.3 μL of LY-6c-PE-Cy7 (Cat. No. 25-5932-82, eBioscience) antibody, 0.3 μL of Ly-6G-PE (Cat. No. 12-9668-82, eBioscience) antibody, 0.625 μL of CD11b-BV605 (Cat. No. 63-0112-82, eBioscience) antibody and 1.25 μL of F4/80-PE-CY 5.5 (Cat. No. 45-4801-82, eBioscience) antibody, incubated on ice in the dark for 20 minutes, washed with an FACS Buffer twice, resuspended to 100 μL of FACS Buffer, and detected on a computer. $CD45^+CD11b^+F4/80^+Ly6G$-Ly6C-cells were labeled as the macrophages. Results were shown in FIG. 6B, and after PYK2 protein expression was inhibited, the formation of the macrophages was significantly inhibited, which suggested that the differentiation of the mouse bone marrow-derived cells into the macrophages could be inhibited by inhibiting the mechanical signal check point PYK2.

Embodiment 6

A Function of a Mechanical Force Sensing Receptor Piezo1 in Regulating and Controlling a Novel Mechanical Force Signal Checkpoint PYK2 was Provided.

The present invention provided the following three human Piezo1 gene inhibitors (siRNA): Si-Piezo1_1: ATGGCCTCTGGGACCATGA (SEQID NO. 4); Si-Piezo1_2: TCCGCCTACCAGATCCGCT (SEQID NO. 5); Si-Piezo1_3: GCCCTCTACCTGCGCAAGA (SEQID NO. 6), and functions of the gene inhibitors in regulating and controlling PYK2 expression and activation of the cells by regulating and controlling a calcium ion signal of the monocytes/macrophages were verified, by specific steps as follows.

1) Transfection of THP-1 cells: the cells were inoculated into a 24-well plate at a density of $2.5 \times 10^5$/well. A transfection reagent was prepared: A: 50 μL of low serum culture medium (Opti-MEM I Reduced Serum Medium, Cat. No. 31985070, Gibco) was added with 3 μL of transfection reagent (Lipofectamine™ RNAiMAX Transfection Reagent, Cat. No. 13778075, Invitrogen). B: 50 μL of low serum culture medium (Opti-MEM I Reduced Serum Medium, Cat. No. 31985070, Gibco) was added with 1 μL of siRNA (RIBO BIO). A and B were mixed and incubated at room temperature for 5 minutes, and 50 μL of the mixture was added with the THP-1 cells to culture overnight.

2) A cell suspension was collected and centrifuged at 1000 rpm and room temperature for 5 minutes, and a supernatant was removed. The solution was added with PMA (50 ng/mL, Cat. No. p1585, Sigma) to induce differentiation for 24 hours, then the cell culture medium was replaced by PBS to continuously culture for 24 hours or 48 hours, and then cell calcium ion inflow, real-time PCR and western blot experiments were carried out respectively.

3) Cell calcium ion inflow experiment: after 48 hours of induction by PMA, the cells were washed with DPBS for three times, added with Fluo 4-AM (5 μM, Cat. No. S1060, Beyotime) and Pluronic F-127 (0.1%, Cat. No. ST501-0.1g, Beyotime), incubated at 37° C. for 30 minutes, washed with DPBS for three times, continuously incubated at 37° C. for 30 minutes, and then observed under a fluorescence microscope by using an FITC channel. Yoda1 is an agonist for Piezo1, the cells were added with Yoda1 (300 nM, Cat. No. HY-18723, MCE), and a fluorescence change before and after adding Yoda1 was recorded. Results were shown in FIG. 7A and FIG. 7B, and si-Piezo1-transfected THP-1 cells could significantly inhibit the calcium ion inflow induced by Yoda1, which suggested that the mechanical force sensing receptor si-Piezo1 could directly regulate and control the calcium ion inflow.

4) Real-time PCR experiment: after 48 hours of induction by PMA, the cells were lysed by using Trizol (Cat. No. 15596026, Invitrogen) to extract RNA. The cDNA synthesis was carried out by using a kit HiScript III RT SuperMix for qPCR (Cat. No. 15596026, Vazyme). The mRNA quantification of Piezo1 and Ptk2b was carried out by using a kit Taq Pro Universal SYBR qPCR Master Mix (Cat. No. Q127, Vazyme) and primers Piezo1_F, Piezo1_R, Ptk2b_F, Ptk2b_R, GAPDH_F and GAPDH_R.

Piezo1_F:
(SEQID NO. 7)
CCTGGAGAAGACTGACGGCTAC;

Piezo1_R:
(SEQID NO. 8)
ATGCTCCTTGGATGGTGAGTCC;

Ptk2b_F:
(SEQID NO. 9)
CATCGTGAAGCTGATCGGCATC;

Ptk2b_R:
(SEQID NO. 10)
TCTTGTTCCGCTCCAGGTAGTG;

GAPDH_F:
(SEQID NO. 11)
GTCTCCTCTGACTTCAACAGCG;

GAPDH_R:
(SEQID NO. 12)
ACCACCCTGTTGCTGTAGCCAA.

Results were shown in FIG. 7C, and the mRNA expressions of Piezo1 and Ptk2b of the si-Piezo1-transfected cells were significantly reduced, which suggested that the si-Piezo1 could significantly inhibit the mRNA expressions of Piezo1 and Ptk2b.

5) Western blot experiment: a cell lysis solution was prepared: an RIPA buffer (Cat. No. 89900, Thermo Scientific) was added with a protease inhibitor (Cat. No. 04693116001, Roche) and a phosphatase inhibitor (Cat. No. 04906837001, Roche). After 72 hours of induction by PMA, the cells were lysed with the cell lysis solution and centrifuged at 12000 rpm and 4° C. for 15 minutes, and a supernatant was a cell protein extract. Protein quantification was carried out by using a BCA protein quantification kit (Cat. No. AP12L025, Life-iLab). The cell protein extract was added with a loading buffer (Cat. No. 1610747, Biorad), incubated at 95° C. for 5 minutes, and then subjected to polyacrylamide gel electrophoresis. Proteins in gel were transferred to an NC membrane (Cat. No. 10600001, GE) by using a rapid transfer solution (Cat. No. WB4600, Suzhou New Cell & Molecular Biotech Co., Ltd.), sealed with 5% skimmed milk powder at room temperature for 1 hours, added with a primary antibody PyK2 (1:2000; Cat. No. ab32571, Abcam), p-PYK2 (1:1000; Cat. No. ab4800, Abcam) and GAPDH (1:10000; Cat. No. ab181602, Abcam) respectively, and incubated at 4° C. overnight. The proteins were washed with TBST for three times, added with a secondary antibody (Cat. No. A0208, Beyotime), and incubated at room temperature for 1 hour. The proteins were exposed and developed by using ECL (Cat. No. S6009S, UElandy (Suzhou) Co., Ltd.). Results were shown in FIG. 7D, the si-Piezo1-transfected cells could significantly inhibit the protein expression and phosphorylation of Ptk2b.

The above experimental results showed that the Piezo1 could respond to a change of extracellular matrix mechanical force by directly regulating and controlling the calcium ion inflow of the monocytes and the macrophages. The Piezo1 could regulate and control the mRNA and protein expression and the protein activation of Ptk2b, which indicated that the Piezo1 was an upstream signal protein of Ptk2b.

Embodiment 7

An Application of a Combined Therapeutic Strategy of Targeting a Novel Mechanical Force Checkpoint PYK2 in Combination with an Immune Checkpoint PD-1 in Treatment of Pancreatic Cancer was Provided, which Comprised Specific Steps as Follows.

1) Ptk2b$^{fl/fl}$ mice and Lyz2-Cre$^{ki/+}$ mice were bred to obtain Ptk2b$^{fl/fl}$Lyz2-Cre$^{ki/+}$ mice with Ptk2b gene knockout in a myeloid system and Ptk2b$^{fl/fl}$ mice as a littermate control for animal experiments.

2) KPC cells under digestive culture were centrifuged at 1000 rpm for 5 minutes, then resuspended with 100 μL of precooled PBS, added with 900 μL of Matrigel (Cat. No. REF354234, CORNING), and mixed evenly to adjust a cell concentration to be $1 \times 10^7$ cells/mL, and the mixed cell solution was sucked with an insulin needle and placed on ice for a pancreas in-situ inoculation experiment. The mice prepared for the experiment were weighed, and anesthetized by an anesthesia machine (with 2.5% isoflurane) after skin preparation on the left lower abdomen of the mice, and after induction anesthesia, the mice were placed in an anesthetic mask to maintain anesthesia (with 2% isoflurane). The skin and the peritoneum of the mice were cut along the lower edge of the left rib after iodophor disinfection, the tail of pancreas was picked up with tweezers to expose the pancreas gently, and 50 μL of mixed KPC cell solution was injected into the pancreas with the insulin needle slowly. After inoculation, the peritoneum and the skin were sutured in sequence, and the mice were put on a heating pad for small animals to recover.

3) After one week, a size and a weight of a pancreatic tumor in the mice were measured, and the size and the weight of the tumor in the mice were measured every other day. When the tumor was about 5 mm in size, a therapeutic drug αPD-1 antibody (In VivoMAb anti-mouse PD-1 (CD279), clone RMP1-14, BioXCell) or a negative control drug Iso antibody (In VivoMAb rat IgG2a isotype control, clone 2A3, BioXCell) started to be intraperitoneally injected. The Ptk2b$^{fl/fl}$Lyz2-Cre$^{ki/+}$ and Ptk2b$^{fl/fl}$ mice were divided into two groups of αPD-1 and Iso, and administrated with the drug once every three days, and after 11 times of administration, the survival of the mice was observed.

Results were shown in FIG. 8, and according to the control group administrated with the negative drug, survival time of the mice with Ptk2b knockout in the myeloid system was significantly prolonged compared with wild-type mice; and compared with the control group administrated with the negative drug, the treatment of the αPD-1 drug could significantly prolong survival time of the wild-type mice and the mice with Ptk2b knockout in the myeloid system suffering from the pancreatic cancer. More importantly, the Ptk2b knockout in combination with the αPD-1 treatment could significantly improve the survival of the mice with the pancreatic cancer.

The embodiments above are only the preferred embodiments for fully describing the present invention, and the scope of protection of the present invention is not limited to this. Equivalent substitutions or transformations made by those skilled in the art on the basis of the present invention are all within the scope of protection of the present invention. The scope of protection of the present invention is subject to the claims.

---

I claim:

1. A pharmaceutical composition comprising a Proline-Rich Tyrosine Kinase 2 (PYK2) inhibitor in combination with a Programmed Cell Death Protein 1 (PD-1) immunosuppressant for treating pancreatic cancer, which PYK2 inhibitor comprises a siRNA or sgRNA/CRISPR specifically targeting Ptk2b and consisting of SEQ ID NO. 1-6, and/or a Cre-loxP gene knock-out reagent with Ptk2b as a target gene PD-1, which immunosuppressant optionally comprises a PD-1 antibody.

2. The application according to claim 1, the PYK2 inhibitor is capable of reducing an elastic modulus of cells or inhibiting differentiation of monocytes into macrophages.

3. The application according to claim 1, wherein the PD-1 immunosuppressant is an αPD-1 antibody.

* * * * *

SEQUENCE LISTING

```
Sequence total quantity: 12
SEQ ID NO: 1           moltype = DNA  length = 19
FEATURE                Location/Qualifiers
source                 1..19
                       mol_type = other DNA
                       organism = synthetic construct
SEQUENCE: 1
ggatcatcat ggaattgta                                              19

SEQ ID NO: 2           moltype = DNA  length = 19
FEATURE                Location/Qualifiers
source                 1..19
                       mol_type = other DNA
                       organism = synthetic construct
SEQUENCE: 2
ggacgaggac tattacaaa                                              19

SEQ ID NO: 3           moltype = DNA  length = 19
FEATURE                Location/Qualifiers
source                 1..19
                       mol_type = other DNA
                       organism = synthetic construct
SEQUENCE: 3
cacatgaagt ccgatgaga                                              19

SEQ ID NO: 4           moltype = DNA  length = 19
FEATURE                Location/Qualifiers
source                 1..19
                       mol_type = other DNA
                       organism = synthetic construct
SEQUENCE: 4
atggcctctg ggaccatga                                              19
```

```
SEQ ID NO: 5              moltype = DNA  length = 19
FEATURE                   Location/Qualifiers
source                    1..19
                          mol_type = other DNA
                          organism = synthetic construct
SEQUENCE: 5
tccgcctacc agatccgct                                                    19

SEQ ID NO: 6              moltype = DNA  length = 19
FEATURE                   Location/Qualifiers
source                    1..19
                          mol_type = other DNA
                          organism = synthetic construct
SEQUENCE: 6
gccctctacc tgcgcaaga                                                    19

SEQ ID NO: 7              moltype = DNA  length = 22
FEATURE                   Location/Qualifiers
source                    1..22
                          mol_type = other DNA
                          organism = synthetic construct
SEQUENCE: 7
cctggagaag actgacggct ac                                                22

SEQ ID NO: 8              moltype = DNA  length = 22
FEATURE                   Location/Qualifiers
source                    1..22
                          mol_type = other DNA
                          organism = synthetic construct
SEQUENCE: 8
atgctccttg gatggtgagt cc                                                22

SEQ ID NO: 9              moltype = DNA  length = 22
FEATURE                   Location/Qualifiers
source                    1..22
                          mol_type = other DNA
                          organism = synthetic construct
SEQUENCE: 9
catcgtgaag ctgatcggca tc                                                22

SEQ ID NO: 10             moltype = DNA  length = 22
FEATURE                   Location/Qualifiers
source                    1..22
                          mol_type = other DNA
                          organism = synthetic construct
SEQUENCE: 10
tcttgttccg ctccaggtag tg                                                22

SEQ ID NO: 11             moltype = DNA  length = 22
FEATURE                   Location/Qualifiers
source                    1..22
                          mol_type = other DNA
                          organism = synthetic construct
SEQUENCE: 11
gtctcctctg acttcaacag cg                                                22

SEQ ID NO: 12             moltype = DNA  length = 22
FEATURE                   Location/Qualifiers
source                    1..22
                          mol_type = other DNA
                          organism = synthetic construct
SEQUENCE: 12
accaccctgt tgctgtagcc aa                                                22
```